United States Patent [19]

Someya et al.

[11] Patent Number: 4,577,515
[45] Date of Patent: Mar. 25, 1986

[54] SAMPLING VALVE FOR USE IN HIGH-SPEED LIQUID CHROMATOGRAPHY

[75] Inventors: Noboru Someya, Chiba; Rikizo Horikawa, Toyama, both of Japan

[73] Assignee: Tokyo Rika Kikai Co., Ltd., Japan

[21] Appl. No.: 622,151

[22] Filed: Jun. 19, 1984

[51] Int. Cl.$^4$ .................. G01N 1/10; G01N 30/20
[52] U.S. Cl. .................. 73/863.73; 73/864.83
[58] Field of Search .......... 73/863.72, 863.73, 864.83, 73/864.84

[56] References Cited

U.S. PATENT DOCUMENTS 2,973,117  2/1961  Conklin ........................ 73/863.73
4,476,731 10/1984  Charney ....................... 73/863.73

Primary Examiner—Stewart J. Levy
Assistant Examiner—Tom Noland
Attorney, Agent, or Firm—Wegner & Bretschneider

[57] ABSTRACT

A sampling valve for use in high-speed liquid chromatography comprising a first stator having therein a sample injection flow passage and a solution flow passage, a second stator (B; G; J) having therein solution flow passages and a discharge passage, and a rotor having therein three or more sample holding bores of different diameter, said rotor being rotatably interposed between said first and second stators.

2 Claims, 8 Drawing Figures

SAMPLING VALVE FOR USE IN HIGH-SPEED LIQUID CHROMATOGRAPHY

FIELD OF THE INVENTION

The present invention relates in general to a sampling valve for use in high-speed liquid chromatography, and in particular to a sampling valve for use in high-speed liquid chromatography comprising a first stator having therein a sample injection passage and a solution flow passage, a second stator having therein a solution flow passage and a discharge passage, and a rotor having a therein sample holding bores and rotably interposed between the first and second stators, wherein the flow passages can be changed over by rotating the rotor by an angle to effect sampling.

BACKGROUND OF THE INVENTION

Sampling valves for use in high-speed liquid chromatography today generally comprise a stator having a sample injection passage and a solution flow passage, and another stator having a solution flow passage and a discharge passage. These stators are fixed to an axis. Between these stators a rotor is rotatably mounted, which is provided with a sample loop and a sample holding bore through which a solvent is normally made to flow. In order to perform analysis the sample is injected into said sample loop by means of a microsyringe, for example, and then the rotor is rotated to connect the sample loop holding the sample to the line of a solvent reservoir, a solvent feeding pump, and a column. The sample is thus introduced into the column.

When it is required to inject a desired amount of the sample, a microsyringe is normally used to meter the sample and to inject it into a part of the sample loop. The use of the microsyringe is advantageous in that it makes it possible to use all of the available amount of the sample. Errors in the metering with the microsyringe however will adversely affect the reproducibility.

SUMMARY OF THE INVENTION

The present invention has been made in view of the fact that a more accurate and well-reproducible metering of a sample can be made by levelling the surface of the sample filled in the sample holding bore. An object of the present invention is to provide a sampling valve for use in high-speed liquid chromatography which permits a sample to be metered into several set amounts by simple operations, serving for accurate and well-reproducible analysis of the sample.

In order to acheve the above object, the sampling valve according to the present invention comprises a first stator having therein a sample injection flow passage and a solution flow passage, a second stator having therein a solution flow passage and a discharge passage, and a rotor having therein a plurality of sample holding bores of different diameter, the rotor being rotatably interposed between the first and second stators.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
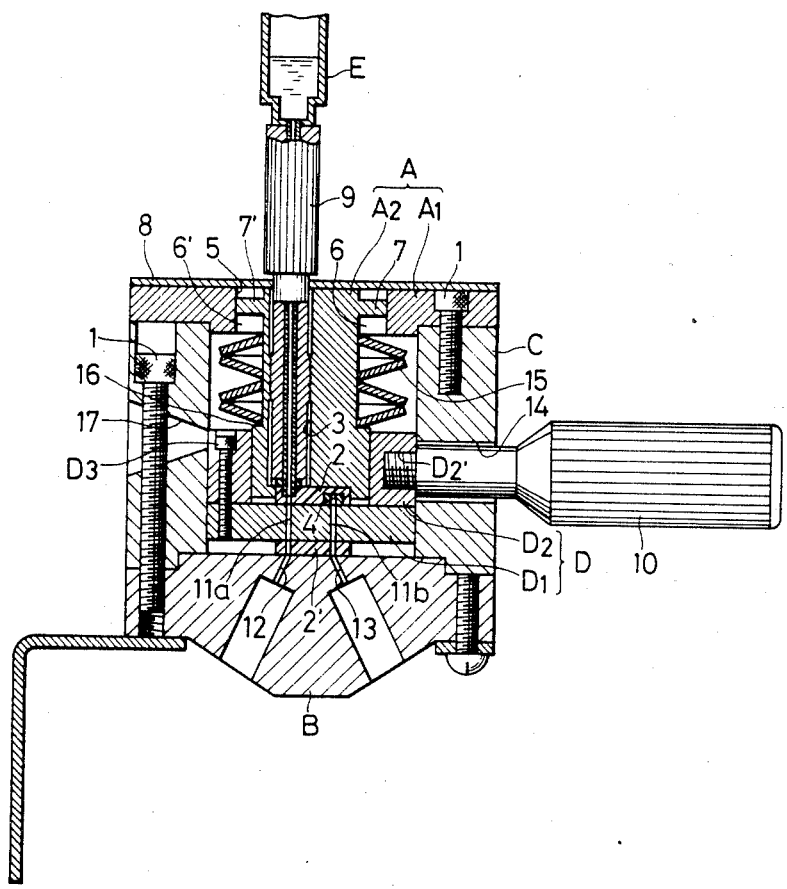
FIG. 1 is a longitudinal sectional view of a first embodiment of the sampling valve of the invention.
Figure 2:
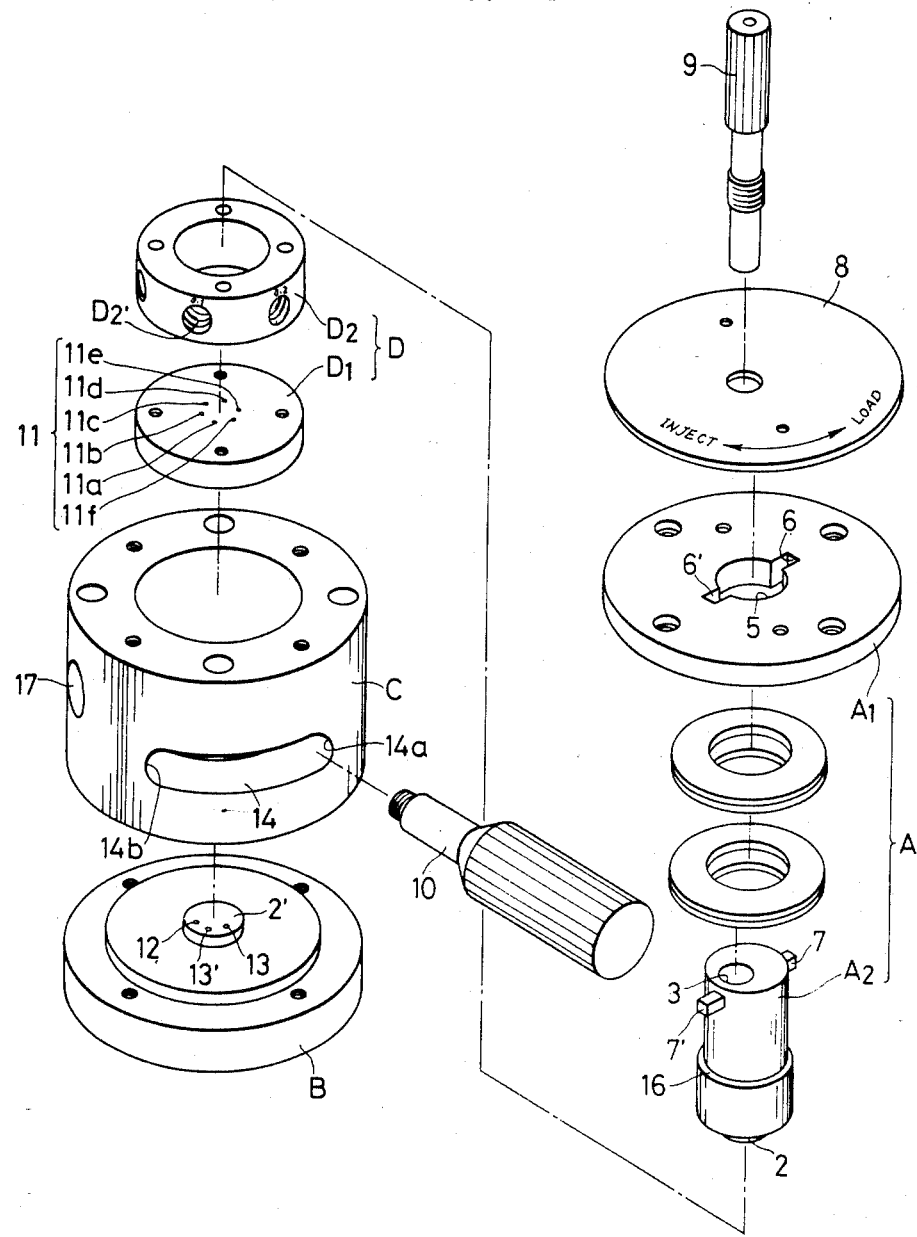
FIG. 2 is an exploded perspective view of the valve of FIG. 1.

Referring first to FIGS. 1 and 2, a first embodiment of the sampling valve comprises a first stator A which consists of a flange member A1 and a stator body A2. A second stator B, which is generally cylindrical and of the same outer diameter with the flange member A1. These stators A and B are fixed to a tubular member C on the opposite sides by means of screws 1 as shown in FIG. 1, the tubular member being of the same outer diameter with the flange member A1. Inside the tubular member C and between the stator body A2 and the second stator B, there is fluid-tightly and slidably mounted a rotor D interposed between packings 2 and 2' of a material such as a synthetic resin fixed to the stator body A2 and the second stator B respectively. The stator body A2 of the first stator A is formed with a sample injection passage 3 and a solution flow passage 4, and has on its top portion a pair of lugs 7 and 7' to be engaged in a pair of depressions 6 and 6', respectively, formed in the inside of a central bore 5 of the flange body A1. The engagement of the lugs and depressions prevents the rotation of the stator body A2 relative to the flange body A1. Further, on the top portion of the first stator A a stator cover 8 and a needle guide 9 for a microsyringe E or a tube (not shown) are provided.

The rotor D comprises a rotor body D1 and a generally cylindrical member D2 fastened together by screws D3. The member D2 surrounds the first stator A, and is adapted to be engaged with a rotating lever 10. The body member D1 is formed with a plurality of, e.g. six, sample holding bores 11a, 11b, 11c, 11d, 11e, and 11f of different or equal diameter. On the other hand, the member D2 is provided with as many mounting holes D2', to which the rotating lever 10 is mounted, as the sample holding bores 11. Each mounting hole D2' is accompanied by a mark above it, which shows e.g. the capacity of the corresponding sample holding bore 11 (0.1 $\mu$l, 0.2 $\mu$l, 0.4 $\mu$l, 0.5 $\mu$l, 1 $\mu$l, for example).

The second stator B is formed with a discharge passage 12 and a pair of solution flow passages 13 and 13', which can be connected with the sample injection passage 3 and the solution flow passage 4, respectively, of the first stator A.

The tubular member C is provided with a slot 14 extending therethrough for limiting the circumferential displacement of the rotating lever 10 screwed into the member D2, to a range which corresponds to the interval between the neighboring sample holding bores 11 formed in the rotor body D1.

Coned disc springs 15, loaded between a shoulder 16 of the stator body A2 and the flange member A1, urges the first stator A toward the second stator B to improve the fluid-tightness provided by the packings 2 and 2' and the rotor body D1, thereby to provide for high-pressure analysis.

Figure 3:
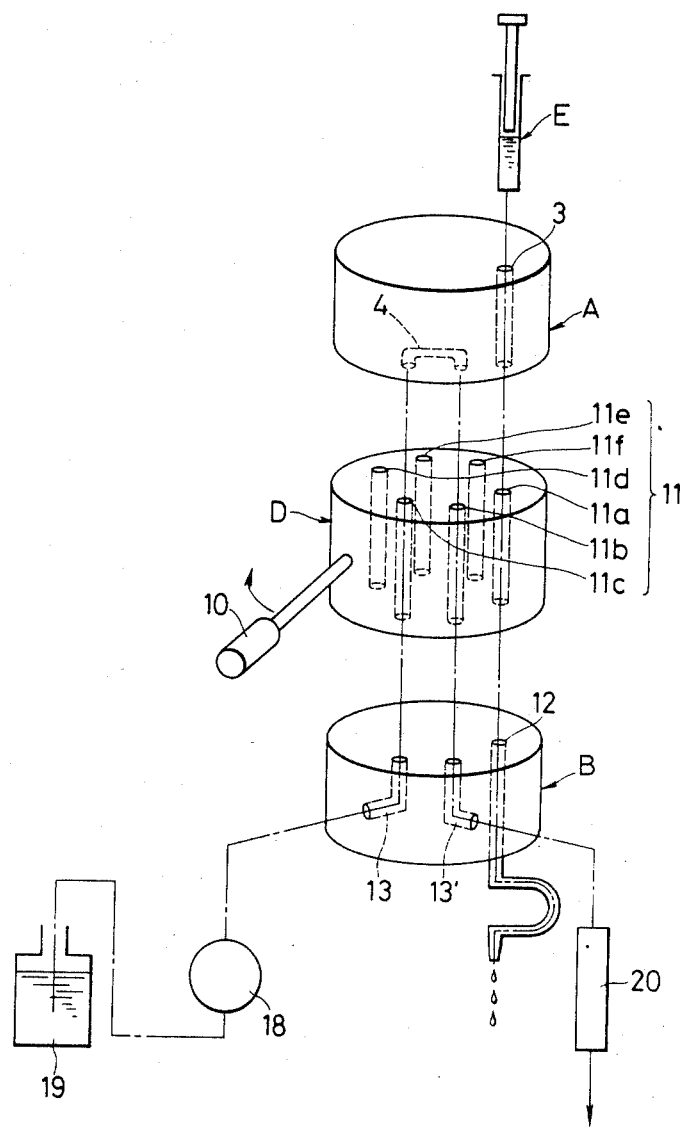
FIG. 3 is a schematic view of the valve of FIG. 1, in which the flow passages are shown.

To make analysis using the sampling valve described above, the user will first identify the mark showing the sample holding bore (e.g. 11a) which has the desired capacity, by observing the mark through a window 17 formed in the tubular member C. If the mark is the desired one, then the rotating lever 10 is mounted to the mounting hole D2' then found near one limit 14a of the slot 14. Then, as shown in FIG. 3, the desired sample holding bore 11a is connected at one end to the sample injection passage 3 of the first stator A, and at the other end to the discharge passage 12 of the second stator B. Then, a pump 18 will feed a solvent from a reservoir 19 into the solution flow passage 13 of the second stator B, from which the solvent flows through the sample holding bore 11c of the rotor D, the solution flow passage 4 of the first stator A, another sample holding bore 11b of the rotor D, another solution flow passage 13' of the second stator B, and then the solvent is introduced into a column 20.

Under these conditions a sample is injected through the sample injection passage 3 into the desired sample holding bore 11a, using a microsyringe E, until the bore is filled. Then the rotor D is rotated by moving the rotating lever 10 to the opposite limit 14b of the slot 14. This rotation will level and thus meter the sample in the bore 11a, while connecting the sample holding bore 11a with the solution flow passages 4 and 13' of the stators A and B respectively, and another bore 11b with the solution flow passages 4 and 13 of the stators A and B respectively. The sample in the bore 11a is thus introduced into the column 20 thogether with the solvent.

There are several sample holding bores 11 of different diameter, so that different volumes of samples may be analyzed in sequence by injecting samples and rotating the rotor D in sequence in the same manner as described above.

The combination of the metering with a microsyringe and the metering with the sample holding bores, will make it possible to fill a sample holding bore with a sample by injecting into it a volume of the sample slightly more than the capacity of such bore. It therefore will ensure accurate metering without wasting too much quantities of samples.

Figure 4:
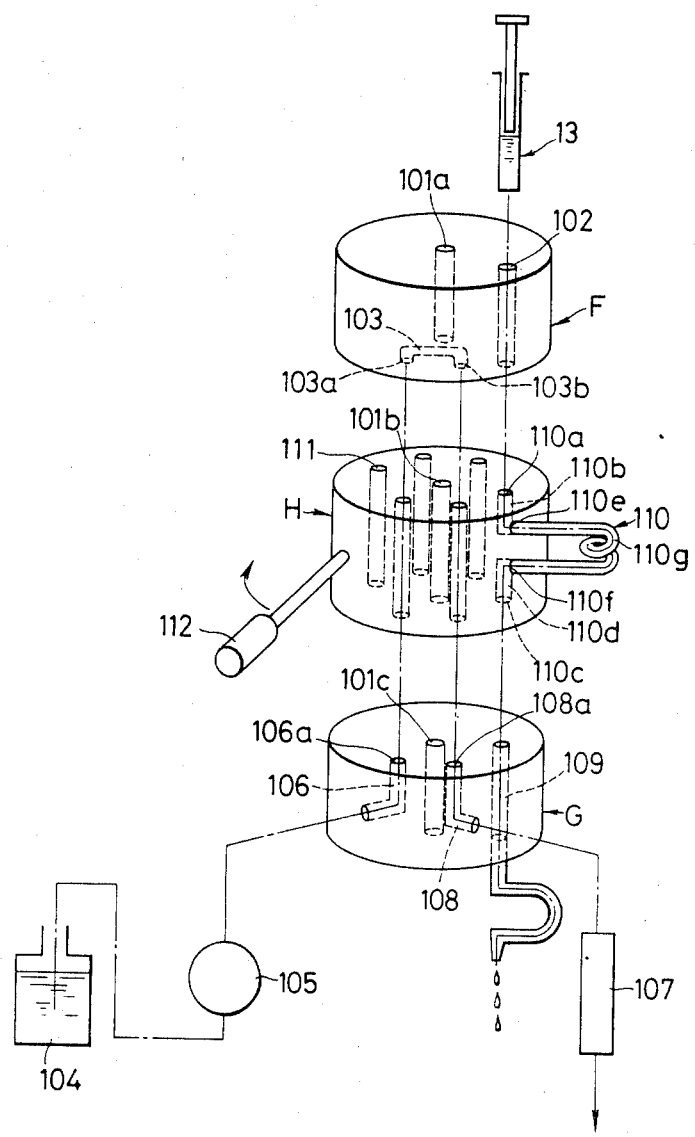
FIG. 4 is a schematic view of a second embodiment of the sampling valve of the invention, in which the flow passages are shown.
Figure 5:
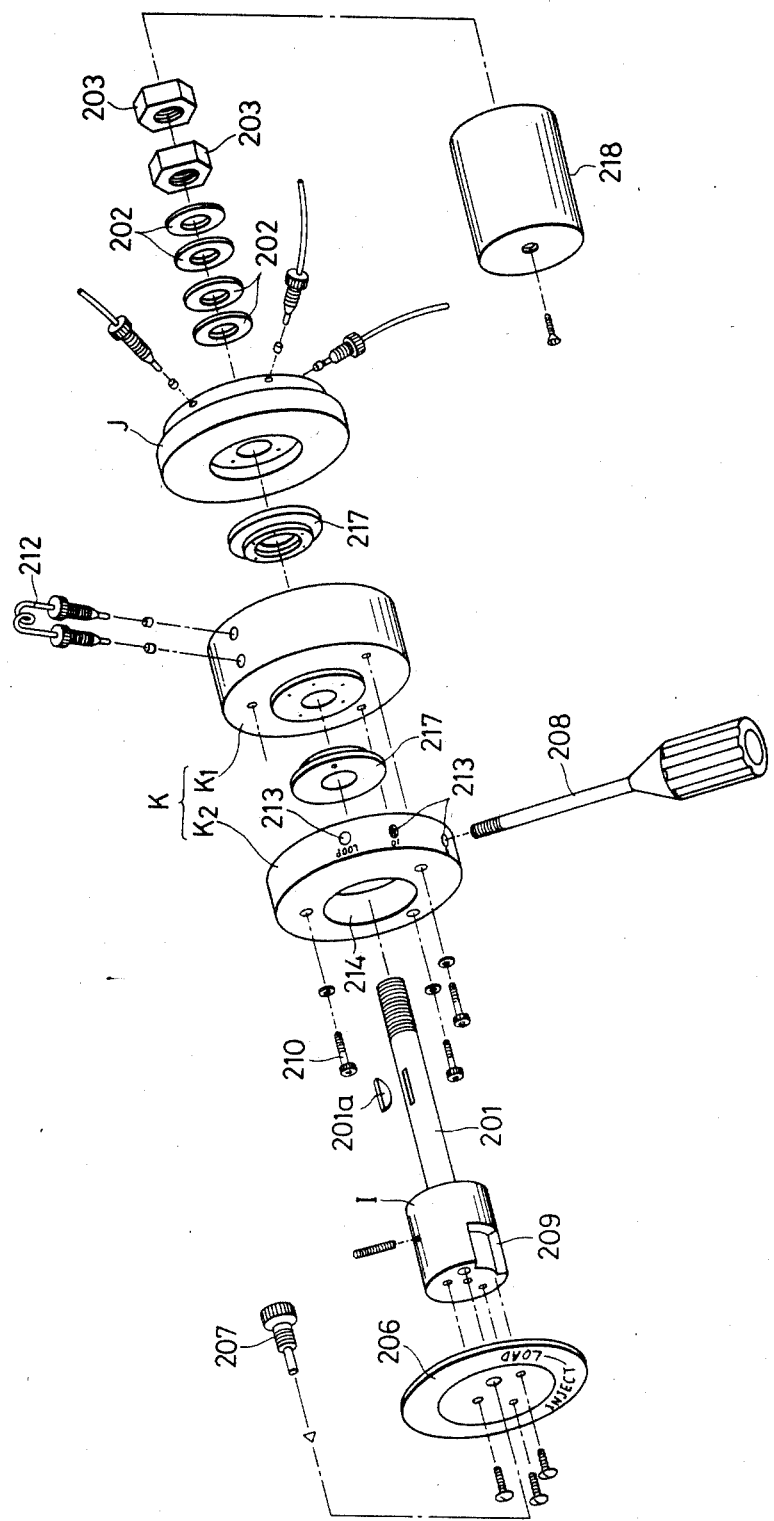
FIG. 5 is an exploded perspective view of a third embodiment of the sampling valve of the invention.
Figure 6:
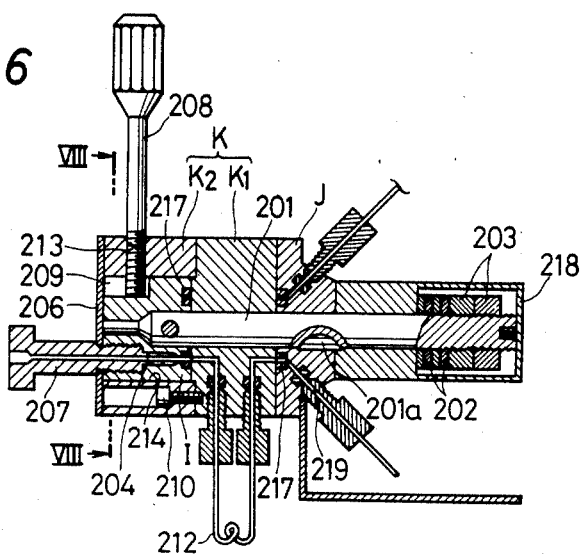
FIG. 6 is a longitudinal sectional view of the valve of FIG. 5.
Figure 7:
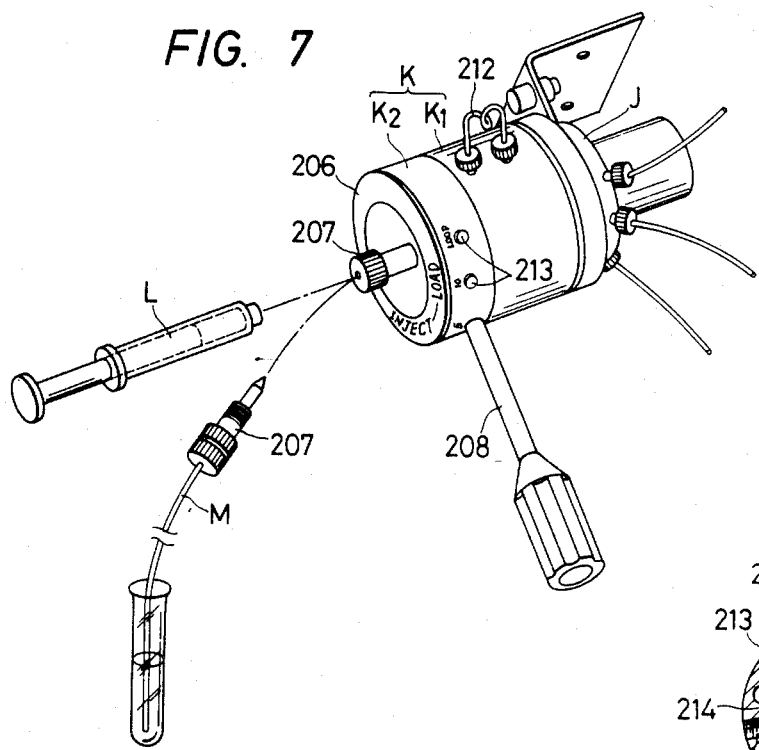
FIG. 7 is a perspective view of the valve of FIG. 5.

FIG. 4 shows another embodiment of the invention. This sampling valve comprises a first and second cylindrical stators F and G, respectively, and a likewise cylindrical rotor H. The first stator F is formed with an axial bore 101a, and a flow passage 103 with both ends open to the rotor H and extending generally perpendicularly to the axial bore 101a. The second stator G is formed with an L-shaped flow passage 106 into which a solvent is pumped from a reservoir 104 by a pump unit 105, another L-shaped flow paasage 108 out of which a solvent or sample flows into a column 107, and a discharge passage 109 parallel with an axial bore 101c; these passages 106, 108, and 109 are configured in a circle and spaced from one another by a distance equal to the distance between the ends 103a and 103b of the flow passage 103 formed in the first stator F.

The rotor H is provided with an axial bore 101b, an L-shaped flow passage 110b with one end 110a open to the first stator F, another L-shaped flow passage 110d with an end 110c open to the second stator G, and sample flow passages 111 parallel with the axial bore 101b. These passages 110b, 110d, and 111 are configured in a circle centered at the axial bore 101b, and are spaced from one another by a distance which is equal to the distance between the ends of the flow passage 103 formed in the first stator F. The sample flow passages 111 are different , in diameter from one another. A tube 110g extending outside the rotor H is connected to the L-shaped flow passages 110b and 110d to form a sample loop 110. A lever 112 is attached to the side of the rotor H, which lever is used to rotate the rotor H.

The stators F and G are fastened to an axial shaft (not shown) in such a manner that the sample injection passage 102 of the first stator F and the discharge passage 109 of the second stator G are aligned with each other, and the ends 103a and 103b of the flow passage 103 of the first stator F are in line with the ends 106a and 108a, respectively, of the flow passages 106 and 108 of the second stator G, which ends 106a and 108a being opposite to the rotor H. Between the stators F and G the rotor H is rotatably mounted on the axis (not shown).

In order to make analysis using the sampling valve, the rotor H is positioned so as to connect the sample injection passage 102 of the first stator F with the sample loop 110 or either of the sample holding bores 111 of the rotor H in FIG. 4 the sample loop 110 is connected). Then, a solvent is pumped by a pump unit 105 from a reservoir 104 into the passage 106 of the second stator G. The solvent flows through the channel formed by the passage 106, the sample holding bore 111 of the rotor H, the passage 103 of the first stator F, another sample holding bore 111 of the rotor H, and the passage 108 of the second stator G. The solvent is thus introduced into a column 107.

Next, a sample is injected into the sample loop 110 through the sample injection passage 102 by means of a microsyringe 113. The excess portion of the sample thus injected is discharged through the discharge passage 109 of the second stator G. The lever 112 is then rotated (in FIG. 4, in the direction indicated by an arrow) to connect the sample loop 110 to the line from the passage end 103b to the passage 108 of the second stator G, thereby to introduce the sample into the column 107 for analysis. There are several sample holding bores 111 of different diameter, so that different volumes of samples may be analyzed in sequence by injecting samples and rotating the rotor H in sequence in the same manner as described above.

With this embodiment, it is possible to determine the sample quantities to injected, by the use of a microsyringe. However, the determination of the sample quantities by the sample holding bores is more advantageous from the view points of accuracy and reproducibility, except when the sample is so valuable that no waste is permitted. Thus, although a microsyringe is used for sample injection in this example, naturally it is also possible to employ other means, such as a tube. Further, the combination of the metering with a microsyringe and the metering with the sample holding bores, will make it possible to fill a sample holding bore with a sample by injecting into it a volume of the sample slightly more than the capacity of such bore. Such combination will therefore ensure accurate metering without wasting too much quantities of samples.

FIGS. 5 to 8 show a third embodiment of the invention. Fixed to a generally cylindrical first stator I is an axial shaft 201 with a threaded end. On this axial shaft 201 a generally cylindrical rotor K is rotatably mounted. A second stator J is fixed under the rotor by spring washers 202 and nuts 203, and by a key 201a to the axis 201.

The first stator I is formed with a sample injection passage 204 and a solution flow passage 205. A stator cover 206 and a needle guide 207 are provided on the top of the stator I, which guide 207 is used for a microsyringe L or a tube M. The top portion of the stator I is formed with an engaging groove 209 on the side, which groove is adapted to engage with the front end 208a of a rotating lever 208 which will be described later.

There will be provided a needle guide 207 adapted for a microsyringe L, and also another needle guide 207 adapted for a tube M. One of these guides will be attached to the stator I.

The rotor K comprises a rotor body K1, and a generally cylindrical mounting member K2 surrounding the first stator I. These members K1 and K2 are fastened together by screws 210. The rotor body K1 is provided with a plurality of sample holding bores 211 of different or equal diameter, and a sample loop 212. The mounting member K2 is provided with the same number of mounting holes 213 with the sample holding bores 211 and the sample loop 212, the rotating lever 208 being mounted to either of these holes. The mounting holes 213 extend through the member K2, opening into a central bore 214 of the member K2 into which the first stator I is inserted. By the holes 213 e.g. the capacities (5 $\mu$l, 10 $\mu$l, LOOP) of the sample holding bores 211 are indicated.

Figure 8:
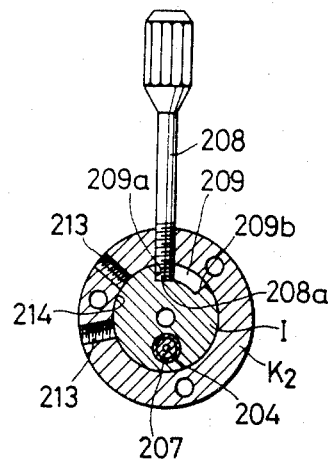
FIG. 8 is a sectional view of the valve of FIG. 5 taken along lines VIII—VIII shown in FIG. 6.

In order to inject a sample into a desired one of the sample holding bores or loop, the sample injection passage 204 of the first stator I will be brought into connection with the desired bore or loop by following the steps of: screwing the front end 208a of the rotating lever 208 into the desired mounting hole, and rotating the rotor K until the front end 208a meets one side wall 209a of the engaging groove 209 formed in the first stator I in the mounting member K2, as shown in FIG. 8. In order to introduce the sample contained in the desired sample holding bore or loop into a column 216, such bore or loop is brought into connection with the line from a solvent reservoir 215 to the column 216 by rotating the rotor K until the front end 208a of the lever 208 meets the opposite side wall 209b of the engaging groove 209.

Sealing members 217 serve to prevent leakage of the sample or solvent at the junctions between the stators I and J and the rotor K. 218 is a cover on the front end of the axis 201, and 219 is a discharge passage.

What is claimed is:

1. A sampling valve for use in a high-speed liquid chromatography comprising a first stator having therein a sample injection flow passage and a solution flow passage; a second stator having therein a solution flow passage and a discharge passage; a rotor having therein three or more sample holding bores of different diameter, said rotor being rotatably interposed between said first and second stators; and an axial shaft fixed between said stators, said axial shaft extending through said rotor in such a manner as to allow said rotor to rotate; either one of said stators or said shaft being provided with a length of engaging groove adapted to engage with a front end of a lever for rotating said rotor; a plurality of mounting holes being provided in such a positions as to permit the adjustment of the angular position of said rotor.

2. A sampling valve for use in high-speed liquid chromatography as claimed in claim 1, in which said stators are fixed with each other by means of a tubular member in which said rotor is rotatably housed; said rotor is provided in the periphery thereof with mounting holes which correspond each to one of said sample holding bores and which is capable of engaging with a rotating lever; said tubular member is provided with a slot for limiting the displacement of said rotating lever in the circumferential direction.

* * * * *